United States Patent [19]

Weissman

[11] 4,380,434
[45] Apr. 19, 1983

[54] DETENT DEVICE FOR A REMOVABLE DENTAL PROSTHESIS

[76] Inventor: Bernard Weissman, 225 E. 48th St., New York, N.Y. 10017

[21] Appl. No.: 251,867

[22] Filed: Apr. 7, 1981

[51] Int. Cl.³ ............................................. A61C 13/22
[52] U.S. Cl. .................................................... 433/177
[58] Field of Search ........................ 433/178, 177, 174

[56] References Cited
U.S. PATENT DOCUMENTS
3,717,931 2/1973 Konig ................................... 433/177

Primary Examiner—Robert Peshock
Attorney, Agent, or Firm—Goodman & Teitelbaum

[57] ABSTRACT

A detent device for removably securing a dental prosthesis in a patient's mouth, having a spring loaded plunger movably disposed in an externally threaded tubular member with an end portion of the plunger projecting outwardly therefrom. A positioning spring member is enclosed in the dental prosthesis for determining the location of the tubular member therein, and for receiving the threads of the tubular member for retention thereof in the dental prosthesis. An externally threaded plug member is engaged in the spring member when the dental prosthesis is being formed to provide an internally threaded opening in the dental prosthesis for receiving the threaded tubular member after the plug member is removed from the dental prosthesis. A dental tool engages a front portion of the tubular member for threading the tubular member into the dental prosthesis to a selected position therein. A longitudinally extending slot is provided across the threads of the tubular member to receive an adhesive for securing the tubular member in the selected position. A recess is provided in a natural tooth of the patient for receiving the plunger therein to removably secure the dental prosthesis in the patient's mouth.

13 Claims, 12 Drawing Figures

{ 4,380,434 }

DETENT DEVICE FOR A REMOVABLE DENTAL PROSTHESIS

BACKGROUND OF THE INVENTION

This invention relates to a removable dental prosthesis, and more particularly to a detent device for securing such removable dental prosthesis in the patient's mouth.

Holding devices for securing removable dental prosthesis in a patient's mouth are well known in the art. These dental prostheses, such as partial dentures or removable bridge work, are inserted in the patient's and must be securely held in place, while at the same time, an appropriate holding device must be provided to permit their removal when desired for cleaning and maintenance thereof. Such holding devices are disclosed in the Applicant's U.S. Pat. Nos. 3,089,242, 3,304,610 and 3,380,161.

U.S. Pat. No. 3,089,242 discloses a device having a ring attached to a T-shaped member which is secured to the dental prosthesis, the T-shaped member and ring being slid downwardly into a channel provided in a member which is secured to a fixed tooth in the patient's mouth for securing the dental prosthesis to the fixed tooth.

U.S. Pat. Nos. 3,304,610 and 3,380,161 disclose detent devices having a spring biased plunger. The detent devices are secured in the artificial tooth so that the plunger can engage a recess provided in a natural tooth in the patient's mouth to secure the dental prosthesis to the natural tooth.

While each of the aforementioned devices provides an appropriate mechanism for retaining a dental prosthesis, the ability to provide an improved retention of the dental prosthesis while at the same time facilitating removal thereof, can be improved upon over prior art devices.

SUMMARY OF THE INVENTION

Accordingly, it is an object of the present invention to provide an improved detent device for retaining a removable dental prosthesis in a patient's mouth which overcomes the disadvantages of the prior art devices.

Another object of the present invention is to provide a reliable detent device for a removable dental prosthesis which prevents any accidental displacement of the prosthesis in the patient's mouth.

Still another object of the present invention is to provide a detent device for a removable denture which secures the prosthesis and at the same time permits a quick and easy removal of the prosthesis from the patient's mouth.

A further object of the present invention is to provide a detent device for a removable dental prosthesis which includes a spring loaded plunger movably disposed in a tubular member, and also includes a positioning spring member enclosed in the dental prosthesis for determining the location of the tubular member and for retaining the tubular member in the dental prosthesis.

Still another object of the present invention is to provide a detent device as described above, which includes adjustment means on the tubular member for permitting the tubular member to be longitudinally moved within the dental prosthesis to a selected position, the tubular member also including securement means for securing the tubular member in the selected position.

Still another object of the present invention is to provide a detent device as disclosed above, and including a tool for engaging the adjustment means of the tubular member for moving the tubular member longitudinally in the dental prosthesis.

Yet a further object of the present invention is to provide a detent device as described above, which includes providing external threaded means on the tubular member to permit threading of the tubular member into the dental prosthesis and also for engagement with the positioning spring member for retention thereof.

Another object of the present invention is to provide a threaded plug member which is received in the positioning spring member when the dental prosthesis is being formed to provide the internal thread in the dental prosthesis for receiving the tubular member of the detent device described above.

Briefly, in accordance with the present invention, there is provided a detent device for removably securing a dental prosthesis in position in a patient's mouth. The detent device includes a spring loaded plunger movably disposed in a tubular member with an end portion of the plunger projecting outwardly therefrom. The tubular member is externally threaded so that it can be threaded into the dental prosthesis. A positioning spring member is enclosed in the dental prosthesis for determining the location of the tubular member therein, and for receiving the threads of the tubular member for retention thereof in the dental prosthesis. An externally threaded plug member is engaged in the spring member and positioned on a frame when the dental prosthesis is being formed to provide an internally threaded opening in the dental prosthesis, after the plug is removed therefrom, for receiving the threaded tubular member therein.

A suitable dental tool engages a front portion of the tubular member for threading the tubular member into the dental prosthesis to a selected position therein. A longitudinally extending slot is provided in the outer surface of the tubular member to receive an adhesive for securing the tubular member in the selected position. A recess is provided in a natural tooth of the patient for receiving the plunger therein to removably secure the dental prosthesis in the patient's mouth.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the accompanying drawings of a preferred embodiment in which.

In the various figures of the drawings, like reference characters designate like parts.

DETAILED DESCRIPTION OF THE PREFERRED EMBODIMENT

Figure 1:
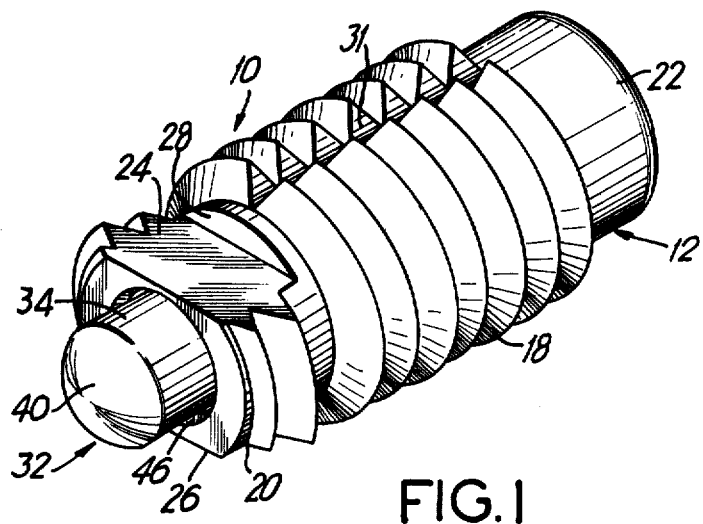
FIG. 1 is a perspective view of the detent device in accordance with the present invention.
Figure 2:
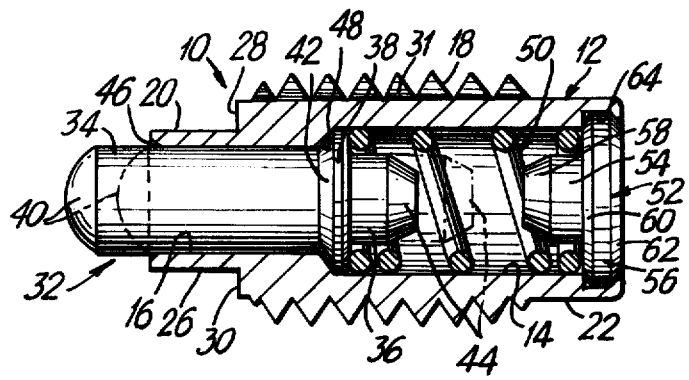
FIG. 2 is a sectional view of the detent device.

Referring now to FIGS. 1 and 2, the detent device is shown generally at 10 and comprises a tubular member 12 having a large diameter bore 14 and a small diameter bore 16 in communication with each other to extend longitudinally through the tubular member 12. The external surface of the tubular member 12 is provided with threads 18 extending from the front portion 20 to a small unthreaded rear portion 22. The front portion 20 is transversely cut to provide two opposed flat parallel surfaces 24, 26 with associated perpendicular shoulders or stop portions 28, 30 spaced from the front end of the tubular member 12, the function of which will be set forth below. Furthermore, a longitudinally extending V-shaped slot 31 is provided across the threads 18, the slot 31 extending downwardly to the root diameter of the threads 18, the function of which will also be set forth below.

A plunger 32 is positioned within the tubular member 12. The plunger 32 includes a large forward cylindrical body section 34 and a small rearward cylindrical body section 36 of smaller diameter, which are joined together by an enlarged circular collar section 38. The body section 34 has a rounded front end 40, the collar section 38 has a beveled edge 42 facing towards the front rounded end 40, and the rear body section 36 has a tapered end portion 44.

The plunger 32 is inserted into the tubular member 12 from the rear portion 22 so that the front cylindrical body section 34 passes through the large bore 14 and is positioned in the small bore 16 with the rounded end 40 extending outwardly therefrom. It is noted, that the front opening of the bore 16 is chamfered at 46, and that the wall between the large bore 14 and the small bore 16 is also chamfered at 48. Accordingly, the beveled edge 42 of the collar section 38 of the plunger 32 abuts against the chamfer 48 between the two bores 14, 16 to limit the outward projection of the forward body section 34.

A coil spring 50, having closed end loops at both ends thereof, is disposed in the large bore 14 with one end mounted onto the rear body section 36 so that the spring end abuts against the plunger collar section 38 as shown in FIG. 2. A cap member 52 closes the rear opened end of the bore 14. The cap member 52 includes a cylindrical body section 54 having a collar section 56 thereon. The body section 54 has a tapered front end 58, and the collar section 56 has beveled edges 60, 62 facing in opposite directions.

Accordingly, a recess 64 is formed in the rear portion 22 of the tubular member 12 at the end of the bore 14 to receive the collar section 56 of the cap member 52 therein. Once the cap member 52 is seated in the recess 64, the end of the rear portion 22 is bent inwardly to capture the cap member 52 therein. The rear end of the spring 52 is disposed around the body section 54 of the cap member 52, with the spring rear end abutting against the collar section 56. Thus, the plunger 32 is captured within the tubular member 12, being free to move axially within the bores 14, 16 against the action of the spring 50, as shown in phantom lines, wherein the forward extent of the plunger is limited by the engagement of the beveled edge 42 of the plunger collar section 38 against the bore chamfer 48 of the tubular member 12.

Figure 3:
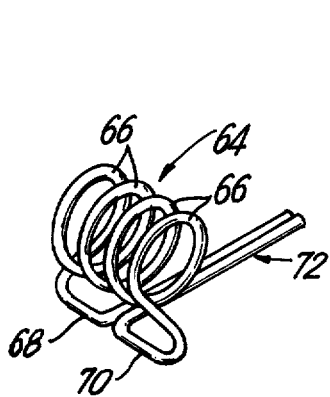
FIG. 3 is a perspective view of a positioning spring member associated with the detent device, in accordance with the present invention.

A positioning spring member 64 is shown in FIG. 3. The spring member 64 includes a series of loops 66, perferably four loops in a helical arrangement having a common longitudinal axis extending therethrough. The opposite ends of the arrangement of the loops 66 are connected to arm sections 68, 70 which extend downwardly from the loop arrangement and then extend towards each other to provide a handle section 72 in which the arm sections 68, 70 are disposed in a side-by-side relationship. The handle section 72 is spaced from the loops 66 and extends perpendicularly to the longitudinal axis of the loops 66 at the mid point of the loop arrangement to define a T-shaped configuration. The helix of the loops 66 correspond to the threads 18 of the tubular member 12 so that the threads 18 can be threadedly received in the loops 66, as will be set forth below.

Figure 4:
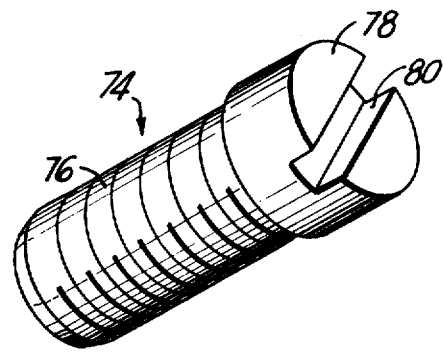
FIG. 4 is a perspective view of a plug member for use with the spring member when the dental prosthesis is being formed.

A plug member 74 is disclosed in FIG. 4. The plug member 74 has a threaded stem portion 76 and an enlarged head portion 78. A slot 80 is provided in the head portion 78. It is noted, that the threads on the stem portion 76 of the plug member 74 are similar to the threads 18 on the tubular member 12, so that the loops 66 of the spring member 64 will also receive the threaded portion 76 of the plug member 74, as set forth below. The stem portion 76 has a length substantially equal to the length of the detent device 10.

Figure 5:
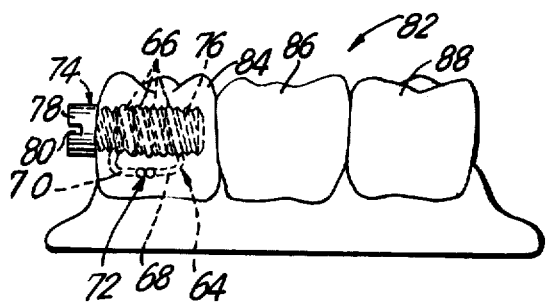
FIG. 5 is a side elevational view of the dental prosthesis showing the spring member and the plug positioned therein.
Figure 6:
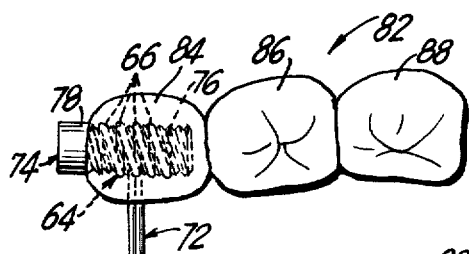
FIG. 6 is a top plan view of the dental prosthesis shown in FIG. 5.

FIGS. 5 and 6 show a dental prosthesis 82 comprising artificial teeth 84, 86 and 88, with the above mentioned plug member 74 and spring member 64 disposed in the artificial tooth 84. Accordingly, before the artificial tooth 84 is formed in a conventional manner well known in the dental art, the spring member 64 is positioned on the dental technician's frame so that the material which will comprise the tooth 84, such as acrylic, can be formed around the spring member 64. Once positioned, the spring member 64 is held in place by conventional means by its handle section 72, and the plug member 74 is threaded into the loops 66 of the spring member 64. The artificial tooth 84 is now built up around the stem portion 76 of the plug member 74 and the spring member 64 so that the head portion 78 of the plug member 74 extends outwardly from the artificial tooth 84 and the handle section 72 extends outwardly from the side of the artificial tooth 84 as shown in FIGS. 5 and 6.

Figure 7:
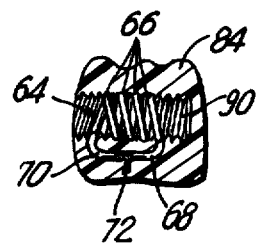
FIG. 7 is a cross sectional view of one tooth of the dental prosthesis showing the spring member disposed therein after the plug member has been removed.

A conventional tool is now disposed in the slot 80 of the plug head portion 78, and the plug member 74 is unthreaded from the artificial tooth 84 and spring member 64 to remove the plug member 74 therefrom. With the plug member 74 removed, the artificial tooth 84 is left with an internally threaded passageway 90 which cooperates with the loops 66 of the spring member 64 which remains fixed in the artificial tooth 84, as shown in FIG. 7.

As shown, the arm sections 68, 70 and a portion of the handle section 72 of the spring member 64 are embedded in the material of the artificial tooth 84 so that the spring member 64 cannot be removed from the artificial tooth 84. It is noted, that the portion of the handle section 72 extending outwardly from the surface of the artificial tooth 84, as shown in FIG. 6, is cut off, and the cut ends still present in the artificial tooth 84 are covered over with the artificial tooth material, such as acrylic. The artificial tooth 84 is now ready to receive the detent device 10, as set forth below.

Figure 8:
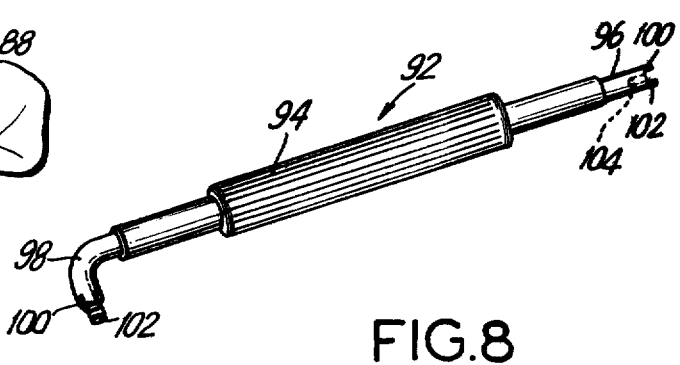
FIG. 8 is a perspective view of a dental tool for inserting the detent device into the dental prosthesis.

A dental tool 92 for inserting the detent device 10 into the artificial tooth 84 is shown in FIG. 8. The dental tool 92 includes a knurled body section 94 having a straight end portion 96 extending outwardly from one end thereof and an L-shaped end portion 98 extending outwardly from the opposite end thereof. The tip of each end portion 96, 98 includes a pair of spaced apart arms 100, 102. The surfaces of the arms 100, 102 facing each other are flat and parallel to each other wherein the spacing between the arms is equal to the distance between the flat surfaces 24, 26 on the front portion 20 of the tubular member 12. Furthermore, a bore 104 is provided in each end portion 96, 98 rearwardly of the arms 100, 102 to receive the forward end section 34 of the plunger 32 as set forth below.

Figure 9:
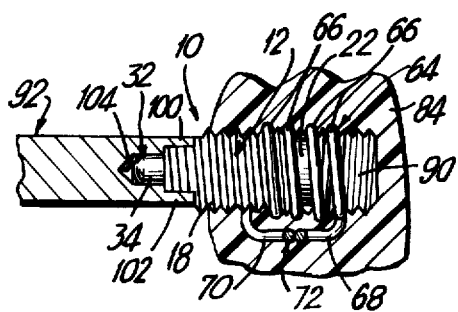
FIG. 9 is a sectional view showing the dental tool inserting the detent device into the dental prosthesis.

As shown in FIG. 9, the arms 100, 102 of the dental tool 92 are positioned on the flat surfaces 24, 26 of the front end portion 20 of the tubular member 12 so that the arms 100, 102 abut against the shoulders 28, 30, and the forward end section 34 of the plunger 32 is received in the bore 104 of the dental tool 92. It is noted, that either end portion 96, 98 of the dental tool 92 may be used by the dental technician, depending upon the manipulation required inserting the detent device 10 in the artificial tooth 84. The detent device 10, being held by the dental tool 92, is now inserted into the passageway 90 in the artificial tooth 84, wherein the unthreaded rear end portion 22 of the tubular member 12 acts as a pilot for guiding the tubular member 12 into the threaded passageway 90. Once positioned, the dental tool 92 is rotated to thread the tubular member 12 into the threaded passageway 90 so that the threads 18 of the tubular member 12 are also engaged by the loops 66 of the spring member 64.

Figure 10:
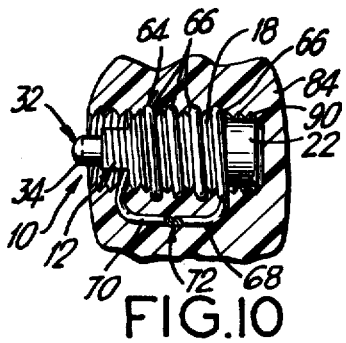
FIG. 10 is a sectional view showing the detent device fully inserted in the dental prosthesis.
Figure 12:
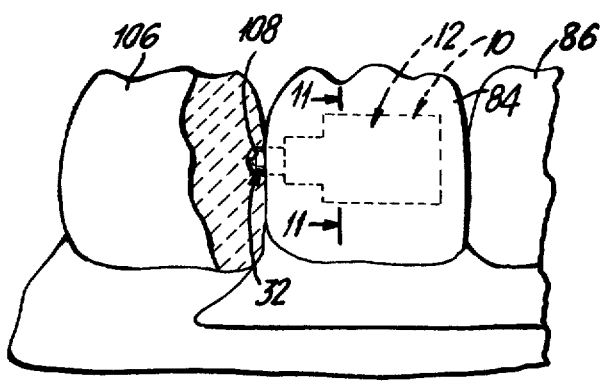
FIG. 12 is a side elevational view, partly in section, showing the dental prosthesis being secured to a natural tooth in the patient's mouth.

FIG. 10 shows the detent device 10 fully inserted in the artificial tooth 84. Accordingly, the dental prosthesis 82 can now be positioned in the patient's mouth so that the artificial tooth 84 is disposed adjacent to the patient's natural tooth 106, wherein a recess 108 is provided in the natural tooth 106 to receive the plunger 32 therein to secure the dental prosthesis 82 in the patient's mouth, as shown in FIG. 12. However, at this point it may be desired to adjust the detent device 10 to provide a secure engagement between the plunger 32 and the tooth recess 108. Thus, the dental prosthesis 82 is removed from the patient's mouth and the dental tool 92 is used to adjust the position of the detent device 10 in the artificial tooth 84 in the same manner as set forth above, wherein the detent device 10 can be moved outwardly or inwardly within the threaded passageway 90 as desired by using the dental tool 92.

Figure 11:
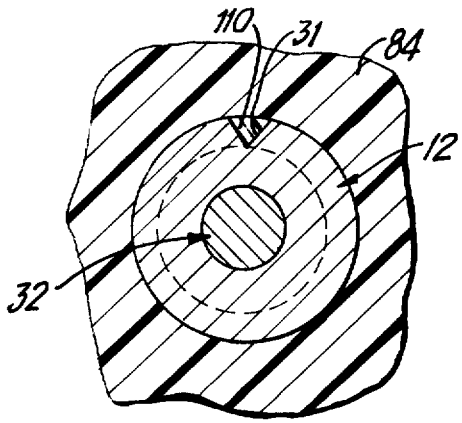
FIG. 11 is a sectional view taken along line 11—11 of FIG. 12.

Once the proper position of the detent device 10 has been selected, an adhesive or cement 110, such as acrylic, is inserted into the V-shaped slot 31 in the tubular member 12 so that the adhesive 110 is secured to the material of the artificial tooth 84, as shown in FIG. 11, to prevent rotation of the tubular member 12 relative to the artificial tooth 84, thereby securing the detent member 10 in the artificial tooth 84 at the selected position. Additional adhesive 110 is also disposed in the front opening of the passageway 90 to finish the construction of the artificial tooth 84, it being noted that this additional adhesive 110 still permits the longitudinal movement of the detent 32.

Preferably, the parts of the detent device 10 and the spring member 64 are fabricated from suitable metal material, wherein the spring member 64 is preferably a one piece construction. The plug member 74 is fabricated from a suitable plastic material.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. A detent device for a removable dental prosthesis, said device comprising:
    a tubular member, said tubular member being externally threaded;
    a spring loaded plunger movably disposed in said tubular member with an end portion of said plunger projecting outwardly from said tubular member;
    stop means within said tubular member for limiting longitudinal movement of said plunger end portion;
    a spring member enclosable in the dental prosthesis when the dental prosthesis is being formed, said spring member determining location of said tubular member in the dental prosthesis and retaining said tubular member in the dental prosthesis;
    said spring member having helical loops;
    said tubular member being inserted through said loops with said loops engaging the external threads of said tubular member; and
    said spring member including securing means for providing a fixed securement of said spring member in the dental prosthesis.

2. A detent device as in claim 1, wherein said securing means includes arm sections extending from opposite ends of said spring member loops, said arm sections joining together to provide a handle section, said arm and handle sections being enclosable in the dental prosthesis.

3. A detent device as in claim 1, including a threaded plug member disposable through said spring member loops with said loops engaging the threads of said plug member when the dental prosthesis is being formed for providing internal threads in the dental prosthesis to receive the threaded tubular member.

4. A detent device as in claim 1, wherein a portion of said tubular member includes a pair of opposing flat parallel surfaces for use in threading said tubular member into the dental prosthesis to a selected position.

5. A detent device as in claim 6, including a tool having spaced apart arms for engaging said flat parallel surfaces of said tubular member to rotate said tubular member for threading into the dental prosthesis.

6. A detent device as in claim 1, wherein a slot is longitudinally disposed across the threads of said tubular member for receiving an adhesive therein to prevent rotation of said tubular member for securing said tubular member in the dental prosthesis at a selected position.

7. A detent device as in claim 1, wherein an end portion of said tubular member is unthreaded to provide a pilot for the threaded portion of the tubular member.

8. A detent device for a removable dental prosthesis, said device comprising:
   a tubular member;
   a spring loaded plunger movably disposed in said tubular member with an end portion of said plunger projecting outwardly from said tubular member;
   stop means within said tubular member for limiting longitudinal movement of said plunger end portion;
   said tubular member including adjustment means for permitting said tubular member to be longitudinally moved in the dental prosthesis to a selected position;
   said tubular member including securement means for securing said tubular member in the dental prosthesis at said selected position;
   said adjustment means including external threads provided on said tubular member for threading said tubular member into the dental prosthesis;
   a spring member having helical loops enclosable in the dental prosthesis;
   said tubular member being inserted through said loops with said loops engaging said external threads of said tubular member to retain said tubular member in the dental prosthesis; and
   said spring member including securing means for providing a fixed securement of said spring member in the dental prosthesis.

9. A detent device as in claim 8, wherein a portion of said tubular member includes a pair of opposing flat parallel surfaces for use in threading said tubular member into the dental prosthesis to the selected position.

10. A detent device as in claim 8, including a tool having spaced apart arms for engaging said flat parallel surfaces of said tubular member to rotate said tubular member for threading into the dental prosthesis.

11. A detent device as in claim 8, wherein said securement means includes a slot longitudinally disposed across said threads of said tubular member for receiving an adhesive therein to prevent rotation of said tubular member in the dental prosthesis at the selected position.

12. A detent device as in claim 8, including a threaded plug member disposable through said spring member loops with the loops engaging the threads of said plug member when the dental prosthesis is being formed for providing internal threads in the dental prosthesis to receive the threaded tubular member.

13. A detent device as in claim 8, wherein said securing means includes arm sections extending from opposite ends of said spring member loops, said arm sections joining together to provide a handle section, said arm and handle sections being enclosable in the dental prosthesis for securing the spring member in the dental prosthesis.

* * * * *